US00PP32075P2

(12) United States Plant Patent
Olesen

(10) Patent No.: US PP32,075 P2
(45) Date of Patent: Aug. 18, 2020

(54) CLIMBING ROSE PLANT NAMED 'POULCY037'

(50) Latin Name: ***Rosa* hybrid**
Varietal Denomination: Poulcy037

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,251

(22) Filed: Sep. 4, 2019

(51) Int. Cl.
*A01H 5/02* (2018.01)
*A01H 6/74* (2018.01)

(52) U.S. Cl.
USPC ..... Plt./133

(58) Field of Classification Search
USPC ..... Plt./133
CPC ..... A01H 5/02; A01H 6/74
See application file for complete search history.

(56) References Cited

PUBLICATIONS

PLUTO Plant Variety Database Mar. 6, 2020. p. 1.*

* cited by examiner

*Primary Examiner* — Annette H Para

(57) ABSTRACT

A new garden rose plant of the Climbing class which has abundant, white flowers and attractive foliage. This new and distinct variety has shown to be uniform and stable in the resulting generations from asexual propagation.

2 Drawing Sheets

Botanical designation: *Rosa* hybrid.
Variety denomination: 'Poulcy037'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulcy037', originated as a single seedling from the stated cross.

The new variety may be distinguished from its male pollen parent and female seed parent primarily by the following characteristics. The male pollen parent plant has orange flowers while the new variety has white flowers. The female seed parent plant has apricot flowers while the new variety has white flowers.

The objective of the hybridization of this rose variety was to create a new and distinct variety with unique qualities, such as:

1. Uniform and abundant white flowers;
2. Vigorous, but compact growth when propagated on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy037' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulcy037' was selected in the spring of 2007 by the inventor as a single plant from the progeny of the aforementioned hybridization.

Asexual reproduction of 'Poulcy037' by rooted cuttings was first done by Mogens N. Olesen in the nursery in Fredensborg, Denmark in July, 2007. This initial and other subsequent asexual propagations conducted in controlled environments have demonstrated that the characteristics of 'Poulcy037' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy037'.

Specifically illustrated in FIG. 1 of the drawings are open flowers at various stages of development, flower petals detached, sepals detached revealing reproductive flower parts, and a cluster of flower buds on the branch.

Figure 1:
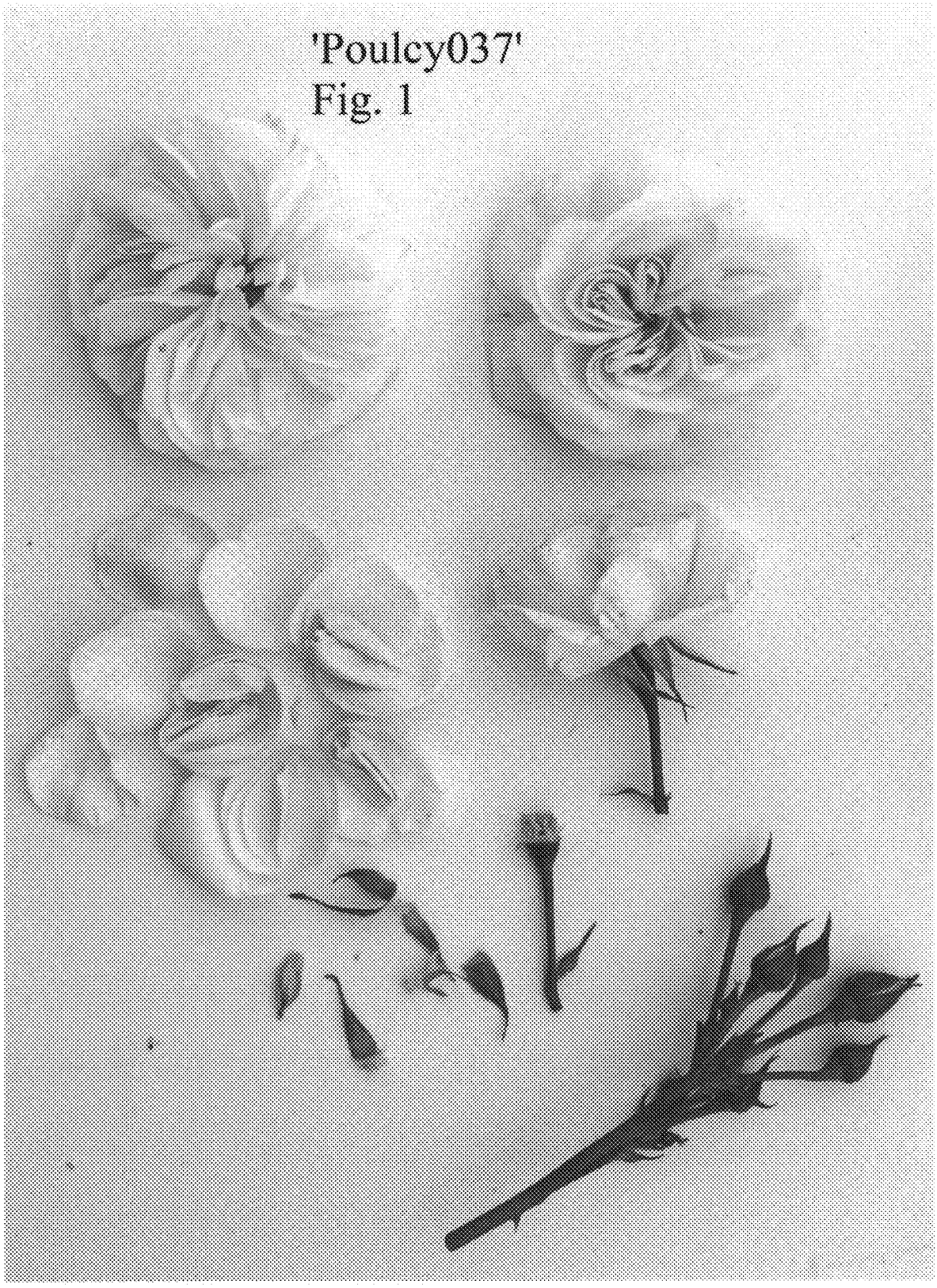
Figure 2:
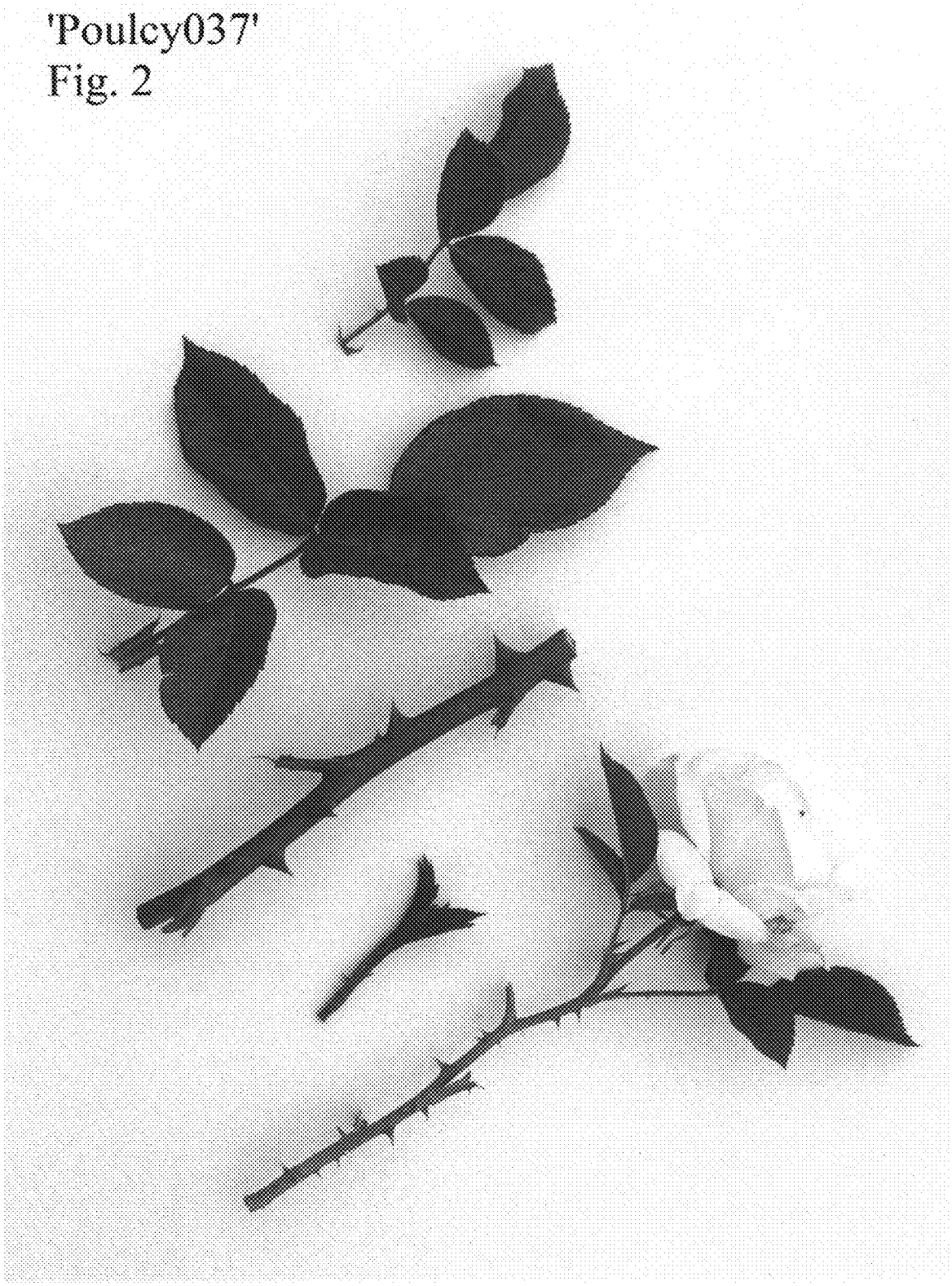

Specifically illustrated in FIG. 2 of the drawings are juvenile and mature leaves, bare stems exhibiting thorns, and an open flower on the branch. Plants shown are 2 years of age.

DETAILED DESCRIPTION OF THE VARIETY

The following is a description of 'Poulcy037', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulslas', United States Plant Patent Application, now abandoned, are compared to 'Poulcy037' in Chart 1.

CHART 1

| | 'Poulcy037' | 'Poulslas' |
|---|---|---|
| Petal Count | 85 to 95 petals | 72 |
| Flower Diameter | 90 mm | 50 mm |
| General Tonality of Flower Color | White Group 155D, with intonations of Orange-White Group 159B | White Group 155C |

Flower and Flower Bud

Blooming habit: Continuous.

Flower bud:

*Size.*—Upon opening, 30 mm in length from base of receptacle to end of bud. Bud diameter is 17 mm.

*Bud form.*—Ovoid.

*Bud color.*—As sepals divide petals are Orange-White Group and White Group 155C.

*Sepal inner surface.*—Color: Yellow-Green Group 146D. Surface: Lightly pubescent.

*Sepal outer surface.*—Color: Yellow-Green Group 144A, with intonations of Greyed-Red Group 182B. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—30 mm long, 8 mm wide.

*Receptacle.*—Texture: Smooth. Size: 9 mm in height, 9 mm wide. Color: Yellow-Green Group 144A. Shape: Funnel.

*Pedicel.*—Surface: Smooth. Length: 30 to 35 mm. Diameter: mm on average. Color: Yellow-Green Group 144B with intonations of Greyed-Red Group 180B. Strength: Strong.

*Peduncle.*—Length: 10 to 20 cm. Diameter: About 4 mm. Color: Yellow-Green Group 145A. Texture: Smooth.

Flower bud development: Flower buds are borne in clusters of about 9 flower buds per stem. Development as a panicle.

Flower bloom:

*Fragrance.*—Moderate.

*Duration.*—The blooms have a duration on the plant of approximately 10 days. Petals fall cleanly away from plant after flowers have fully matured.

*Size.*—Flower diameter is 90 mm when open. Flower depth is 40 mm.

*Flower shape.*—Quartered-rosette, very double, with many overlapping petals packed into quarter sections.

*Shape of flower, side view.*—The upper portion is flat convex. The lower portion is concave.

Petalage: Under normal conditions, flowers have about 85 to 95 petals.

General tonality of flower: Open flowers are White Group 155D, with intonations of Orange-White Group 159B.

Petal color:

*Outer petals.*—Upper surface: White Group 155C. Lower surface: White Group 155C.

*Upon opening, inner petals.*—Upper surface: White Group 155C, with intonations of Orange-White Group 159A. Lower surface: White Group 155D, with intonations of Orange-White Group 159B.

*Basal petal spots.*—No distinctive coloration at the petal base observed.

Petals:

*Petal reflex.*—Somewhat reflexed.

*Margin.*—Entire and uniform. Moderate undulations.

*Shape.*—Round. Apex shape: Rounded. Base shape: Rounded.

*Size.*—38 mm (l)×40 mm (w).

*Texture.*—Smooth.

*Thickness.*—Average.

Petaloids:

*Size.*—22 mm (l) by 20 mm (w).

*Quantity.*—5 or 6.

*Shape.*—Elliptical with an acute base and rounded apices.

*Color.*—Upper surface is White Group 155C, with intonations of Orange-White Group 159A. The lower surface White Group 155D, with intonations of Orange-White Group 159B.

Reproductive flower parts:

*Pollen.*—None observed.

*Anthers.*—Size: 2 mm in length. Color: Yellow Group 4D. Quantity: 35 on average.

*Filaments.*—Color: Yellow Group 4B. Length: 6 mm.

*Pistils.*—Length: 6 mm. Quantity: 20 on average.

*Stigmas.*—Color: Green Yellow Group 1C.

*Styles.*—Color: Green Yellow Group 1C.

*Location of stigmas.*—Inferior in location relative to the length of the filaments and the height of the anthers.

*Hips.*—None Observed.

Plant

Plant growth: Climbing and bushy. Plants are 120 to 150 cm in height, and 100 cm wide.

Stems:

*Color of juvenile growth.*—Yellow-Green Group 144B.

*Color of mature growth.*—Yellow-Green Group 144A.

*Length.*—Canes are about 45 cm from the base of the plant to the flowering portion.

*Diameter.*—About 7 mm.

*Internodes.*—On mature canes about 45 to 55 mm between nodes.

*Surface texture.*—Young wood: Smooth. Older wood: Smooth.

Long prickles:

*Incidence.*—9 prickles per 10 cm of stem.

*Size.*—Average length of prickles on mature stems is 9 mm.

*Shape.*—Upper portion is linear. Lower portion is concave.

*Color.*—Juvenile prickles: Greyed-Orange Group 174B. Mature prickles: Greyed-Orange Group 174B.

Plant foliage:

*Compound leaf.*—180 mm (l)×120 (w).

*Quantity.*—3 leaves per 10 cm of stem on average.

*Leaf bearing angle to the stem.*—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 11 mm long, mm wide. Quantity: 2 per compound leaf. Shape: Linear, slightly broad based with outward extending apices. Margins: Finely serrated. Color:

*Petiole*.—Length: 20 mm. Diameter: 2 mm. Upper surface color: Yellow-Green Group 144A. Lower surface color: Yellow-Green Group 144A.

*Rachis*.—Length: 70 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 85 mm long, 50 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Climbing rose class named 'Poulcy037', substantially as illustrated and described herein, due to its abundant white flowers, disease resistance, and extended period of bloom.

* * * * *

'Poulcy037'

'Poulcy037'